United States Patent
Liu et al.

(10) Patent No.: US 11,273,277 B2
(45) Date of Patent: Mar. 15, 2022

(54) FACE MASK ASSEMBLY

(71) Applicant: BMC MEDICAL CO., LTD., Beijing (CN)

(72) Inventors: Yuanxiang Liu, Beijing (CN); Zhi Zhuang, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 261 days.

(21) Appl. No.: 15/739,323

(22) PCT Filed: Jan. 12, 2016

(86) PCT No.: PCT/CN2016/070622
§ 371 (c)(1),
(2) Date: Dec. 22, 2017

(87) PCT Pub. No.: WO2016/206365
PCT Pub. Date: Dec. 29, 2016

(65) Prior Publication Data
US 2019/0001094 A1    Jan. 3, 2019

(30) Foreign Application Priority Data
Jun. 23, 2015   (CN) .......................... 201510350159.0

(51) Int. Cl.
*A61M 16/06*     (2006.01)
*A61M 16/08*     (2006.01)

(52) U.S. Cl.
CPC ...... *A61M 16/0644* (2014.02); *A61M 16/065* (2014.02); *A61M 16/0683* (2013.01);
(Continued)

(58) Field of Classification Search
CPC ............ A61M 16/0644; A61M 16/065; A61M 16/0655; A61M 16/0638; A61M 16/0633;
(Continued)

(56) References Cited

U.S. PATENT DOCUMENTS 4,620,813 A * 11/1986 Lacher .................. F16C 11/106
248/182.1
4,980,805 A * 12/1990 Maglica ................. F16M 11/14
362/191
(Continued)

FOREIGN PATENT DOCUMENTS

CN          2685947 Y      3/2005
CN      101282767 A     10/2008
(Continued)

*Primary Examiner* — Joseph D. Boecker
*Assistant Examiner* — Brian T Khong
(74) *Attorney, Agent, or Firm* — Volpe Koenig (57) ABSTRACT

A face mask assembly, including: a frame, including a frame body, the frame body being provided with an air intake port; a connecting member, including a first end hingedly connected to the air intake port and a second end having a forehead support fixedly mounted thereon; the second end of the connecting member is used for communication with an air intake tube; the forehead support include a fitting part that fits to the forehead, a mounting part fixedly mounted on the second end of the connecting member, and a connecting part connecting the fitting part and mounting part.

9 Claims, 6 Drawing Sheets (52) U.S. Cl.
CPC ..... *A61M 16/0825* (2014.02); *A61M 16/0616* (2014.02); *A61M 16/0622* (2014.02)

(58) Field of Classification Search
CPC .......... A61M 16/0825; A61M 16/0816; A61M 16/0683; A61M 16/0616; A61M 16/0622; A61M 16/0605; A61M 2016/0661; F16C 11/06; F16C 11/106; F16C 11/0623; F16C 11/0638; F16C 11/0604; F16C 11/0614; F16C 23/045
See application file for complete search history.

(56) References Cited

U.S. PATENT DOCUMENTS

| | | | | |
|---|---|---|---|---|
| 5,897,417 | A * | 4/1999 | Grey | A63H 33/062 446/125 |
| 5,921,239 | A * | 7/1999 | McCall | A61M 16/06 128/205.25 |
| 6,113,301 | A * | 9/2000 | Burton | B60Q 1/0683 362/515 |
| 6,494,635 | B1 * | 12/2002 | Merlo | F16C 11/106 403/103 |
| 6,702,502 | B1 * | 3/2004 | Graber | F16C 11/0638 384/283 |
| 7,857,727 | B2 * | 12/2010 | Rung | B25J 17/0275 403/76 |
| 8,246,266 | B2 * | 8/2012 | Lang | B60R 1/066 359/874 |
| 2003/0074066 | A1 * | 4/2003 | Errico | A61F 2/442 623/17.14 |
| 2003/0147688 | A1 * | 8/2003 | Hathaway | F16C 11/0619 403/90 |
| 2005/0150497 | A1 * | 7/2005 | Eifler | A61M 16/06 128/206.21 |
| 2005/0155603 | A1 * | 7/2005 | Frerichs | A61M 16/0633 128/206.21 |
| 2006/0207599 | A1 | 9/2006 | Busch et al. | |
| 2006/0283458 | A1 | 12/2006 | Woodard et al. | |
| 2007/0044804 | A1 * | 3/2007 | Matula | A61M 16/0638 128/206.21 |
| 2008/0066745 | A1 * | 3/2008 | Janbakhsh | A61M 16/06 128/200.24 |
| 2008/0072910 | A1 * | 3/2008 | Janbakhsh | A61M 16/06 128/206.27 |
| 2008/0314390 | A1 * | 12/2008 | Kwok | A61M 16/0683 128/207.11 |
| 2010/0012128 | A1 | 1/2010 | Takishita et al. | |
| 2011/0305504 | A1 * | 12/2011 | Yu | F16C 11/0604 403/124 |
| 2012/0063840 | A1 * | 3/2012 | Yu | F16C 11/0614 403/141 |
| 2012/0138061 | A1 * | 6/2012 | Dravitzki | A61M 16/0633 128/205.25 |
| 2012/0285452 | A1 * | 11/2012 | Amirav | A61M 16/049 128/203.29 |
| 2013/0000646 | A1 * | 1/2013 | Haibach | A61M 16/06 128/205.25 |
| 2014/0174446 | A1 | 6/2014 | Prentice et al. | |
| 2015/0047640 | A1 | 2/2015 | Mccaslin | |
| 2015/0077630 | A1 * | 3/2015 | Miller | H04N 5/2251 348/376 |
| 2015/0328422 | A1 * | 11/2015 | Chodkowski | A61M 16/06 128/206.21 |
| 2016/0008558 | A1 * | 1/2016 | Huddart | A61M 16/06 128/205.25 |
| 2016/0067442 | A1 * | 3/2016 | Salmon | A61M 16/0683 128/205.25 |
| 2016/0325067 | A1 * | 11/2016 | Harwood | A61M 16/0875 |
| 2016/0341244 | A1 * | 11/2016 | Tonomori | F16C 11/0609 |

FOREIGN PATENT DOCUMENTS

| | | |
|---|---|---|
| CN | 201239409 Y | 5/2009 |
| CN | 102834138 A | 12/2012 |
| CN | 103052421 A | 4/2013 |
| CN | 204050593 U | 12/2014 |
| CN | 204193249 U | 3/2015 |
| CN | 104587580 A | 5/2015 |
| CN | 104906676 A | 9/2015 |
| CN | 204890881 U | 12/2015 |
| EP | 2078534 A1 | 7/2009 |
| EP | 3254721 A1 | 12/2017 |
| JP | 2011104096 A | 6/2011 |
| WO | 2004021960 A2 | 3/2004 |
| WO | 2006138345 A1 | 12/2006 |
| WO | 2013156910 A1 | 10/2013 |
| WO | 2014168489 A1 | 10/2014 |

* cited by examiner

FACE MASK ASSEMBLY

CROSS REFERENCE TO RELATED APPLICATION

This application is a 371 National Stage application of International Patent Application No. PCT/CN2016/070622, which was filed Jan. 12, 2016 and claims priority to Chinese Patent Application No. CN201510350159.0, which was titled as "Face Mask Assembly" and was filed on Jun. 23, 2015, both of which are incorporated herein by reference as if fully set forth.

FIELD OF THE INVENTION

The present invention relates to a respiratory assistance apparatus, in particular to a face mask assembly.

BACKGROUND OF THE INVENTION

It is known to all that face mask assemblies (or referred to as respiratory masks) are mainly applied in continuous positive airway pressure (CPAP) treatment of various respiratory diseases or sleep related breathing disorders. A face mask assembly usually is connected to a respirator so as to supply the respirable air outputted from the respirator to the wearer.

Since the face mask assembly has to be worn for a long time, the wearing comfortability has great influence on the user's experience. A face mask assembly equipped with a forehead support can be borne on the forehead part of the wearer, so that the forehead provides support to alleviate the pressure of the face mask assembly on the face part of the wearer. However, the forehead support on an existing face mask assembly is complex in structure and is inconvenient for the wearer to adjust it to adapt to the height of his/her forehead when the wearer wears the face mask assembly.

SUMMARY OF THE INVENTION

The technical problem to be solved in the present invention is that the forehead support on an face mask assembly in the prior art is complex in structure and is inconvenient for the wearer to adjust it to adapt to the height of his/her forehead when the wearer wears the face mask assembly.

To solve the problem described above, the present invention provides a face mask assembly, which comprises: a frame, comprising a frame body provided with an air intake port; a connecting member, comprising a first end hinged to the air intake port and a second end having a forehead support fixedly mounted thereon and configured to communicate with an air intake tube; the forehead support comprising a fitting part that can be fitted to the forehead, a mounting part fixedly mounted on the second end of the connecting member, and a connecting part connecting the fitting part and the mounting part.

In an embodiment, the outer surface of the first end of the connecting member is a truncated spherical surface, and the air intake port is ball-hinged to the first end of the connecting member.

In an embodiment, the first end of the connecting member includes a first limiting part arranged on the outer surface, the inner surface of the air intake port includes a second limiting part fitted with the first limiting part, and the first limiting part and the second limiting part are fitted with each other to prevent the connecting member from rotating within the air intake port around the axis of the air intake port.

In an embodiment, the first limiting part is a first flat surface or concave spherical surface, the second limiting part is a second flat surface fitted with the first flat surface or a convex spherical surface fitted with the concave spherical surface.

In an embodiment, the first limiting part is a groove extending in the axial direction of the connecting member; the second limiting part is a first protrusion arranged on the inner surface of the air intake port and fitted with the groove.

In an embodiment, the outer surface of the first end of the connecting member is arranged with a second protrusion extending in the circumferential direction around the axis of the truncated spherical surface, the second protrusion is disposed on one side or two sides of the groove, and the inner surface of the air intake port is arranged with a snap slot fitted with the second protrusion.

In an embodiment, the mounting part of the forehead support has a mounting hole, and the second end of the connecting member is fixedly fitted in the mounting hole.

In an embodiment, a limiting member is arranged on the surface of the forehead support that faces the frame body near the lower end of the mounting part.

In an embodiment, the limiting member is a spring.

In an embodiment, the face mask assembly further comprises an elastic member arranged in the clearance formed between the connecting part of the forehead support and the frame body.

The face mask assembly according to the present invention comprises a frame and a forehead support that works with a frame body of the frame. The forehead support is connected to the frame via a connecting member. The connecting member is hinged to an air intake port on the frame, so that the connecting member can swing in the air intake port. The swinging of the connecting member can drive the forehead support fixedly arranged on the second end of the connecting member to swing.

Thus, when a wearer wears the face mask assembly, the wearer may adjust the forehead support automatically by swinging the forehead support according to the height of his/her forehead. Such a manner of adjustment is simple, convenient, and quick. In addition, the forehead support is adapted to different forehead heights of different wearers by swinging, thereby satisfying the requirements of different wearers.

BRIEF DESCRIPTION OF DRAWINGS

Hereunder the present invention will be further detailed in embodiments with reference to the accompanying drawings.

BRIEF DESCRIPTION OF THE SYMBOLS

11—frame body; 111—second flat surface; 112—air intake port; 113—spherical surface; 12—forehead support; 121—upper headgear hook; 122—lower headgear hook; 123—protruding post; 124—mounting hole; 125—supporting frame; 13—connecting member; 131—first flat surface; 132—spherical surface; 133—cylindrical surface; 134—groove; 1341—bottom; 1342—side; 135—second protrusion; 14—cushion; 15—elbow assembly; 16—elastic member; 98—swing direction of connecting member; 99—swing direction of forehead support.

In the drawings, identical components are labeled with the same symbol. The drawings are not drawn to scale.

DETAILED DESCRIPTION OF THE EMBODIMENTS

Hereunder the present invention will be detailed with reference to the accompanying drawings.

Figure 1:
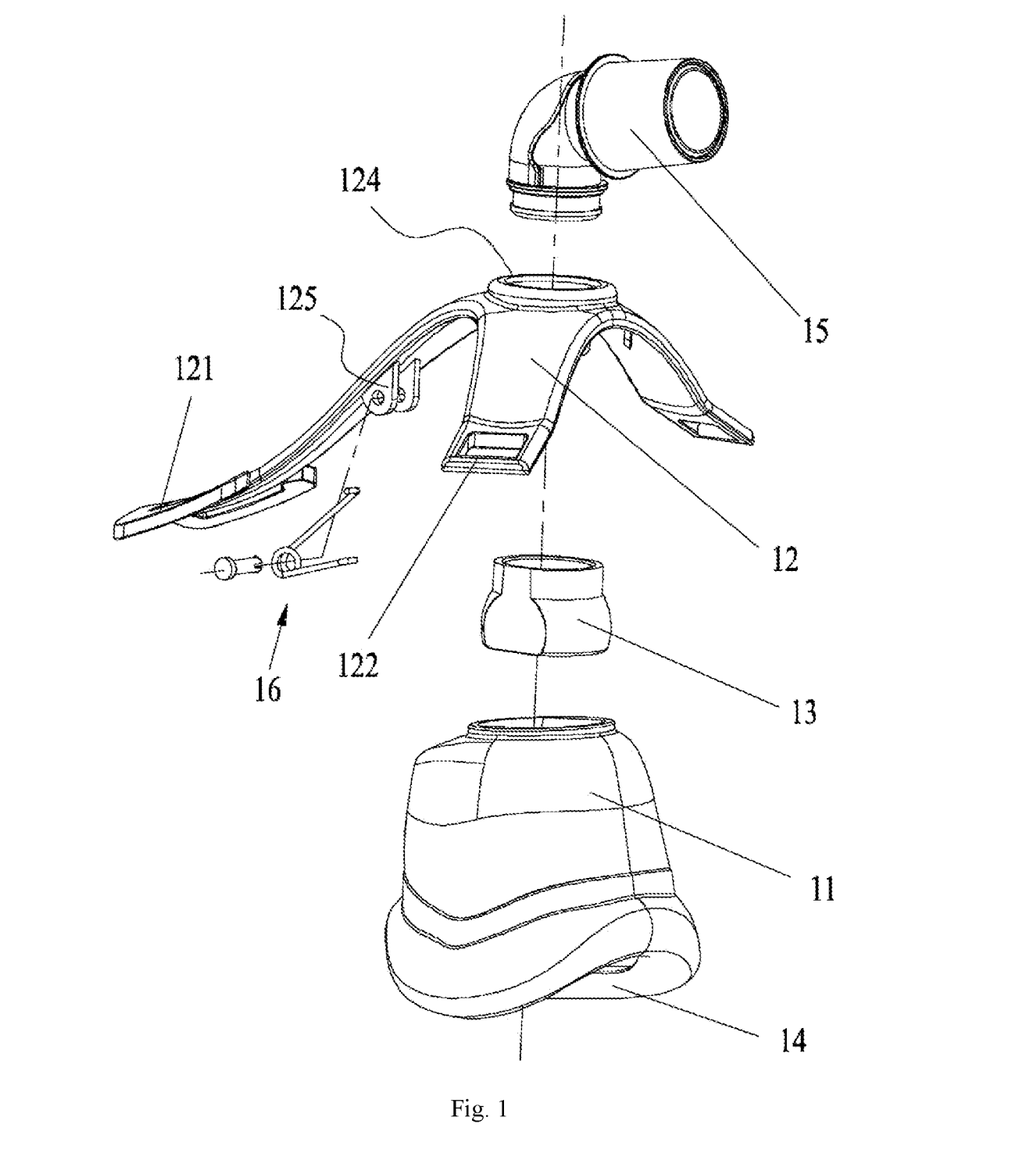
FIG. 1 is an exploded structural view of the face mask assembly according to the present invention.
Figure 2:
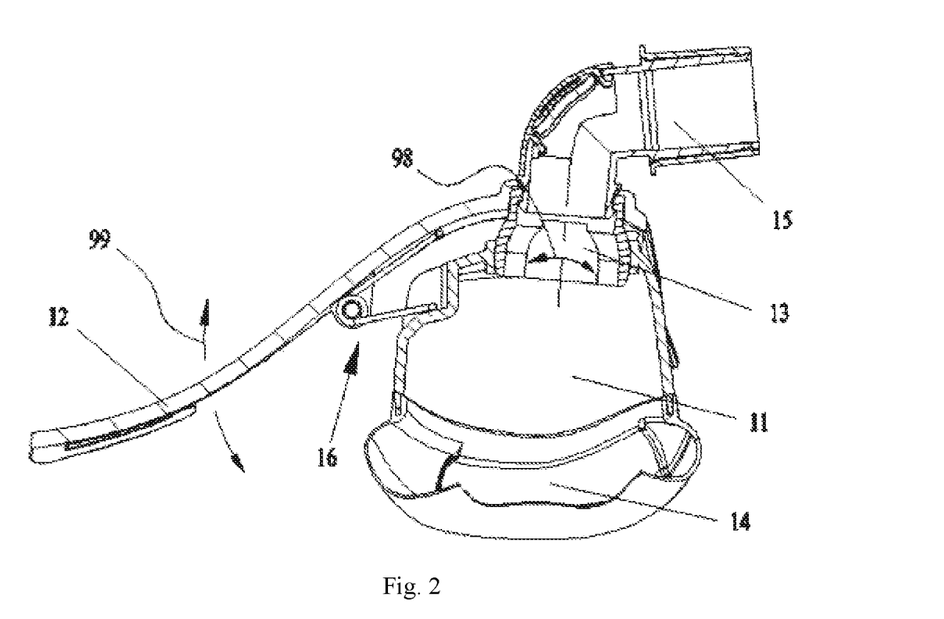
FIG. 2 is a complete sectional view of the face mask assembly in FIG. 1 after the face mask assembly is assembled.

FIGS. 1 and 2 illustrate the structure of an embodiment of the face mask assembly according to the present invention.

As shown in FIGS. 1 and 2, an embodiment of the face mask assembly in the present invention comprises a frame and a forehead support 12. The frame comprises a cushion 14 and a frame body 11 connected to the cushion 14. The frame body 11 and the cushion 14 may be arranged separately and connected by clamping or bonding, etc.; or they can be formed integrally by secondary rubber coating. The cushion 14 is made of a flexible material, so that it can contact with the skin of human better and the wearer feels more comfortable, and can fit the skin well to ensure air tightness. The frame body 11 is configured to connect to the external member. The frame body 11 can accept pressure applied externally and transfer the pressure to the cushion 14. The forehead support 12 is arranged on the periphery of the frame body 11. An upper headgear hook 121 is arranged on the upper end of the forehead support 12.

A lower headgear hook 122 is arranged on the lower end of the forehead support 12. The upper end of the forehead support 12 is a fitting part in this embodiment. The wearer can wear the face mask assembly on his/her face part and adjust the tightness of the headband for several times as required, till there is no air leakage and the face part has no sense of pressure. The wearer may operate the forehead support 12 to swing it close to or away from his/her forehead (in the swing direction 99 shown in FIG. 2), and finally swing the fitting part of the forehead support 12 to a position where the fitting part fits the height of his/her forehead and then fix the headband to his/her head.

Under the tension effect of the headband, the face mask assembly is fixed. Now, the fitting part (at the end where the upper headgear hook 121 is arranged) of the forehead support 12 presses the forehead of the wearer. After the fitting part of the forehead support 12 comes into contact with the forehead of the wearer, the forehead bears a part of the tension force from the upper headband, and thereby the pressure of the face mask on the most sensitive parts at the two sides of the bridge of the nose is decreased, and the wearer who wears the face mask assembly feels more comfortable.

The face mask assembly in this embodiment further comprises a connecting member 13. The connecting member 13 comprises a first end that has a truncated spherical outer surface and a second end that has a cylindrical outer surface. A truncated spherical surface refers to the outer surface of a sphere between two parallel planes when the sphere is truncated by the two parallel planes. An air intake port 112 arranged on the frame body 11 is ball-hinged to the first end of the connecting member 13. The forehead support 12 comprises a fitting part that can be fitted to the forehead, a mounting part fixedly mounted on the second end of the connecting member 13, and a connecting part connecting the fitting part and the mounting part.

In this embodiment, the mounting part is a mounting hole 124. The forehead support 12 is connected to the second end of the connecting member 13 via the mounting hole 124. The forehead support 12 is connected to the frame body 11 via the connecting member 13. An air intake tube of a elbow assembly 15 is connected to the second end of the connecting member 13. Clearance is reserved between the forehead support 12 and the outer surface of the frame body 11 so as to provide certain swing space for the forehead support 12.

Furthermore, to prevent the first end of the connecting member 13 from rotating in the air intake port 112, a first limiting part and a second limiting part are arranged on the connecting member 13 and the inner surface of the air intake port 112 respectively. The first end of the connecting member 13 includes the first limiting part arranged on the outer surface. The inner surface of the air intake port 112 includes the second limiting part that is fitted with the first limiting part. The first limiting part and the second limiting part work together to prevent the connecting member 13 from rotating around the axis of the air intake port 112 in the air intake port. Thus, the swinging of the first end of the connecting member 13 in the air intake port 112 (in the swing direction 98 shown in FIG. 2) drives the forehead support 12 to swing in relation to the frame body 11, so that the wearer can easily actuate the forehead support 12 to swing. After the forehead support 12 is connected to the frame body 11 via the connecting member 13, when the wearer wears the face mask assembly, the forehead support 12 can swing in a plane, and the fitting part of the forehead support 12 gets close to or away from the forehead of the wearer as the forehead support 12 swings. Thus, the forehead support 12 can be swung to different amplitudes to adapt to different forehead heights.

Figure 3:
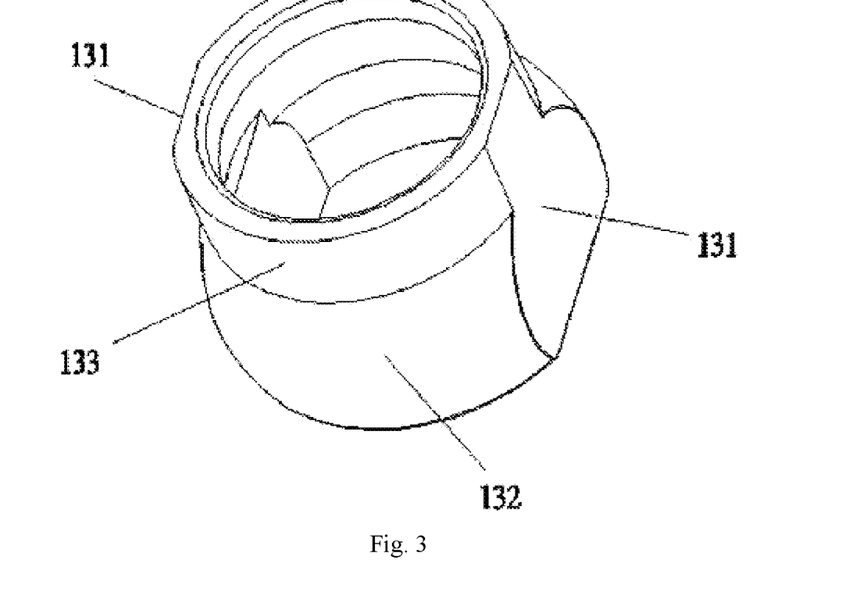
FIG. 3 is a schematic structural diagram of the connecting member in a first embodiment of the present invention.
Figure 4:
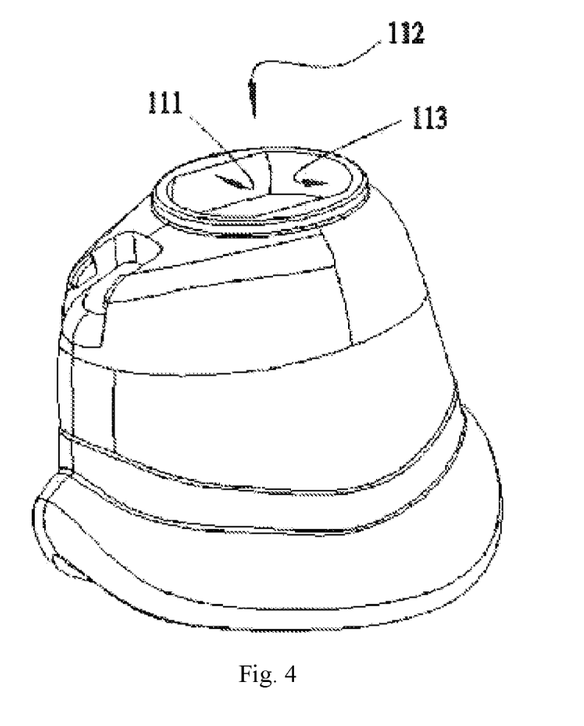
FIG. 4 is a schematic structural diagram of the frame in the present invention.

In an embodiment, as shown in FIG. 3, the outer surface of the connecting member 13 is configured to consist of two first flat surfaces 131 parallel to each other and a spherical surface 132 arranged between the two first flat surfaces 131 and connected to the first flat surfaces 131. The first flat surfaces 131 are first limiting parts. In other embodiments, only one first flat surface 131 may be arranged. As shown in FIG. 4, the inner surface of the air intake port 112 arranged on the frame body 11 has a second flat surface 111 fitted with the first flat surface 131. The second flat surface 111 is a second limiting part. The first flat surface 131 and the second flat surface 111 work with each other to limit the range of movement of the connecting member 13, so that the connecting member 13 can only swing in the air intake port 112 (in the swing direction 98 shown in FIG. 2), but can't rotate around the axis of the air intake port 112 in the air intake port 112.

In an embodiment, as shown in FIG. 3, the outer surface of the connecting member 13 is configured to consist of two concave spherical surfaces that are in axial symmetry and a spherical surface between the two concave spherical surfaces. The centers of sphere of the two concave spherical surfaces 132 are in the same line, and the connecting line between the centers of sphere is perpendicular to the axis of the connecting member 13. The concave spherical surfaces are the first limiting part. In other embodiments, only one concave spherical surface may be arranged. The inner surface of the air intake port 112 arranged on the frame body 11 has convex spherical surfaces fitted with the concave spherical surfaces. The convex spherical surfaces are the second limiting part. Two convex spherical surfaces are arranged opposite to each other, and are fitted with the concave spherical surfaces to clamp the connecting member 13. The connecting member 13 can rotate around the connecting line between the centers of sphere of the two concave spherical surfaces.

When the wearer wears the face mask assembly, the forehead support 12 may be actuated to swing under the tension effect of the headband, so as to adjust the forehead support 12 to an appropriate position. Since the forehead support 12 connected to the connecting member 13 can only swing, the wearer only has to adjust the forehead support 12 in one direction, and the forehead support 12 will not rotate and cause loss of contact of the fitting part with the forehead. Therefore, the wearer can adjust the forehead support 12 simply and quickly, and the difficulty in the adjustment operation is reduced.

As shown in FIG. 4, the inner surface of the air intake port 112 also has a spherical surface 113 fitted with the spherical surface 132 of the connecting member 13. After the spherical surface 132 is fitted with the spherical surface 113 and the first limiting part is fitted with the second limiting part, the connecting member 13 is connected to the frame body 11 and will not fall off from the frame body 11. The connecting member 13 can be separated from the frame body 11 only if enough external force is applied on the connecting member 13.

In an embodiment, the forehead support 12 is formed integrally with the connecting member 13. The forehead support 12 is detachably connected to the frame body 11. When the connecting member 13 is mounted to the frame body 11, the part of the connecting member 13 that has the spherical surface 132 is inserted into the air intake port 112 on the frame body 11. Thus, the mounting procedure is simplified, and the efficiency of assembly is improved.

Figure 5:
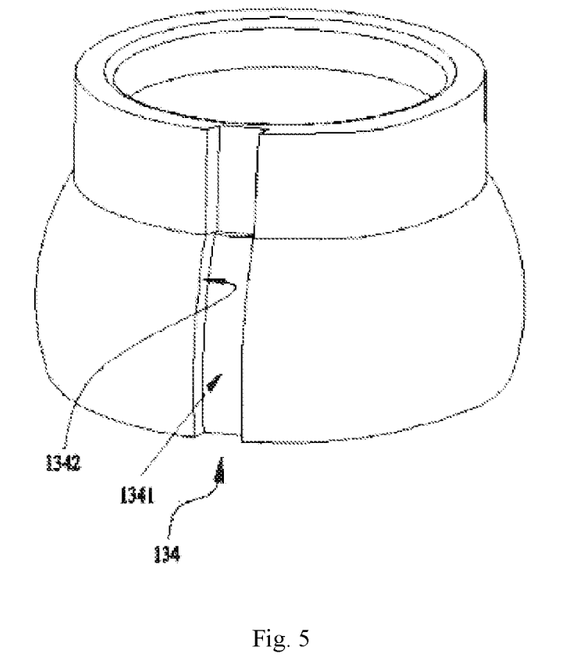
FIG. 5 is a schematic structural diagram of the connecting member in a second embodiment of the present invention.
Figure 6:
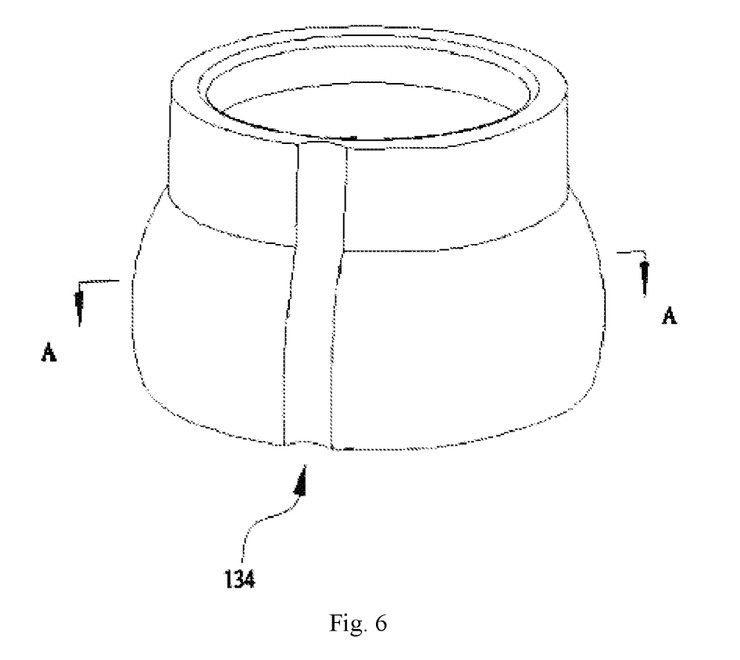
FIG. 6 is a schematic structural diagram of the connecting member in a third embodiment of the present invention.
Figure 7:
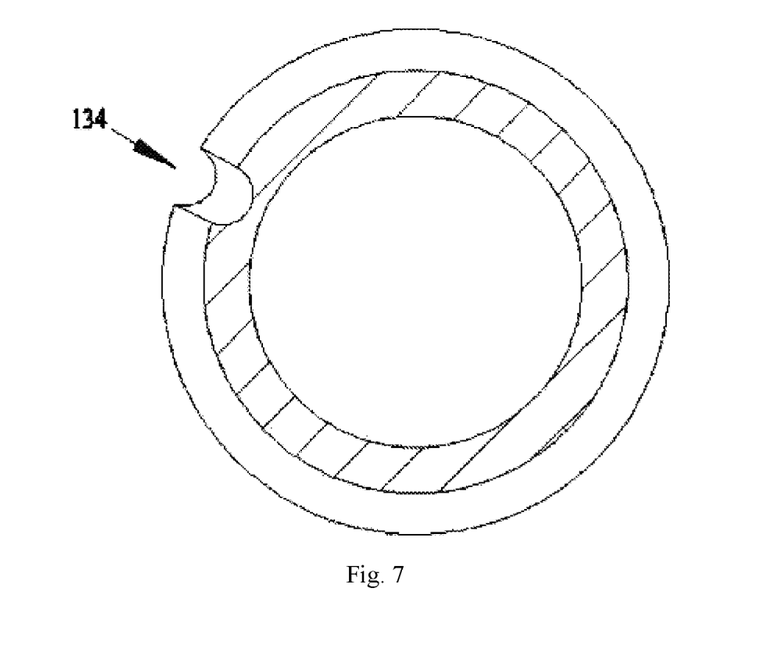
FIG. 7 is a sectional view A-A of the structure in FIG. 6.

In an embodiment, as shown in FIG. 5, the first limiting part is a groove 134 arranged on the periphery of the connecting member 13. The groove 134 extends in the axial direction of the connecting member 13. The peripheral surface of the connecting member 13 is a spherical surface, except for the opening part of the groove 134. In this embodiment, as shown in FIG. 5, the bottom 1341 of the groove 134 is perpendicular to the sides 1342 of the groove 134, and the bottom 1341 is configured to be a spherical surface that has the same center of sphere as the spherical surface arranged on the connecting member 13, or, as shown in FIGS. 6 and 7, the profile of the cross section of the groove 134 is an arc shape.

The inner surface of the air intake port 112 is arranged with a first protrusion (not shown) that is fitted with the groove 134. The first protrusion is the second limiting part. Owing to the sliding fit between the first protrusion and the groove 134 and the limitation of the frame body 11 on the connecting member 13, the connecting member 13 can only swing in the groove 134, but can't rotate around the axis of the air intake port 112 in the air intake port 112.

When the wearer wears the face mask assembly, the wearer may adjust the forehead support 12 connected to the connecting member 13 by hand. Thus, the forehead support 12 will actuate the connecting member 13. At that point, the first protrusion on the frame body 11 slides relatively in the groove 134 of the connecting member 13. In that way, the fitting part of the forehead support 12 can get close to or away from the forehead by swinging, so that the wearer can adjust the fitting part of the forehead support 12 conveniently to a position where the forehead support fits the forehead height.

Figure 8:
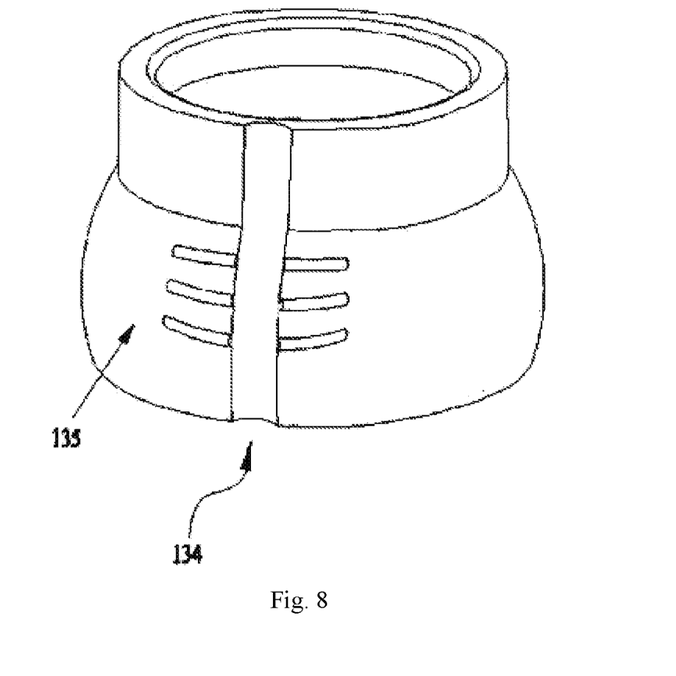
FIG. 8 is a schematic structural diagram of the connecting member in a fourth embodiment of the present invention.

In an embodiment, as shown in FIG. 8, the spherical surface of the connecting member 13 is arranged with a plurality of second protrusions 135 extending around the axis of the connecting member 13. The plurality of second protrusions 135 are arranged at an interval in the axis direction of the connecting member 13 respectively. The inner surface of the air intake port 112 on the frame body 11 is arranged with snap slots (not shown) that are fitted with the second protrusions 135. Wherein, in the case that a plurality of second protrusions 135 are arranged at an interval in the axis direction of the connecting member 13 respectively, one or more snap slots may be arranged.

When the wearer wears the face mask assembly and adjusts the forehead support 12, the second protrusions 135 will be inserted into the snap slot and thereby lock the forehead support 12 in position. Compared with a scheme of interference fit between the spherical surface 132 of the connecting member 13 and the spherical surface 113 of the air intake port 112, the fitting scheme used here can further improve positional stability of the forehead support 12. The position of the connecting member 13 in relation to the air intake port 112 can be adjusted by applying certain external force.

The face mask assembly further comprises an elastic member 16 arranged on the forehead support 12.

The elastic member 16 is arranged between the frame body 11 and the forehead support 12, specifically, the elastic member 16 is arranged in the clearance formed between the connecting part of the forehead support and the frame body 11. The elastic member 16 is closer to the fitting part of the forehead support 12. The forehead support 12 transfers the pressure to the frame body 11, and the frame body 11 transfers the pressure to the cushion 14, so as to increase the pressure of the cushion 14 on the face part of the wearer and enhance the air tightness of the cushion 14.

In this embodiment, the elastic member 16 is a torsional spring. A supporting frame 125 is arranged on the surface of the connecting part of the forehead support 12 that faces the frame body. A pivot hole is arranged in the supporting frame 125. A pin shaft is mounted in the pivot hole, and the torsional spring is fitted over the pin shaft. One leg of the torsional spring abuts against the forehead support 12, and the other leg of the torsional spring abuts against the outer surface of the frame body 11.

In other embodiments, the elastic member 16 may be an elastic gasket or spring fixedly arranged between the connecting part of the forehead support 12 and the outer surface of the frame body 11.

Figure 9:
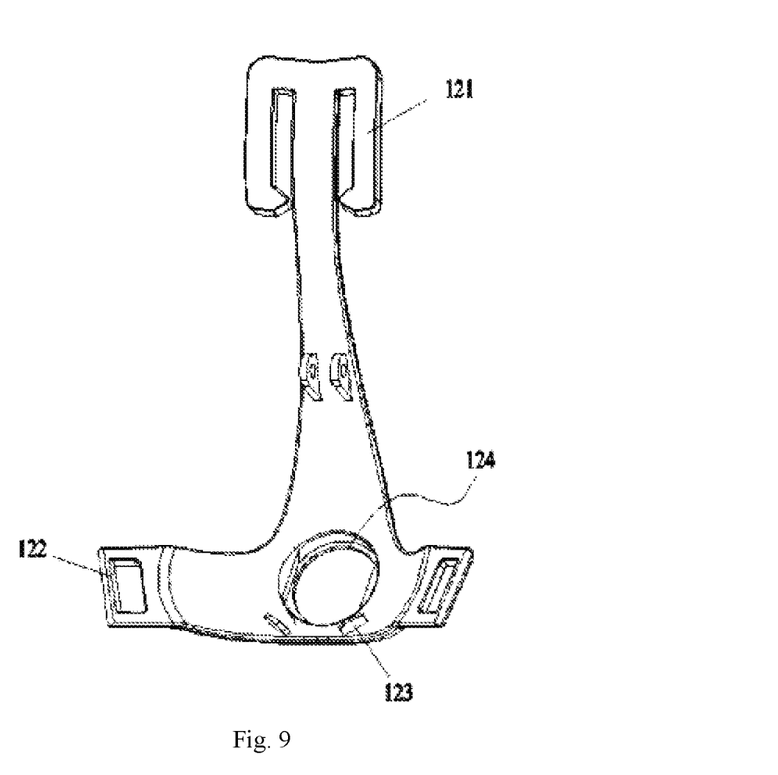
FIG. 9 is a schematic structural diagram of an embodiment of the forehead support in the present invention.

As shown in FIG. 9, a limiting member is arranged on the surface of the forehead support 12 that faces the frame body 11 near the lower end of the mounting hole 124, to limit the swinging range of the forehead support 12.

In an embodiment, the limiting member is arranged on the inner surface near the lower end (the end where the lower headgear hook 122 is arranged) of the forehead support 12. The limiting member is a protruding post 123 extending towards the frame body 11. In a natural state when the face mask assembly is not worn by the wearer, the elastic member 16 is still in a compressed state, and the restoring force of the elastic member 16 acts on the forehead support 12. Therefore, the protruding post 123 presses the surface of the frame body 11, and thereby the forehead support 12 and the elastic member 16 are kept in a stable state in relation to each other. In addition, the protruding post 123 can prevent an excessively wide swinging range of the forehead support 12.

In an embodiment, the limiting member is a spring arranged between the inner surface near the lower end of the forehead support 12 and the outer surface of the frame body 11. When the face mask assembly is not worn by the wearer, the elastic member 16 is still in a compressed state, and the restoring force of the spring acts on the forehead support 12. Therefore, the spring on the forehead support 12 is in flexible contact with the frame body 11 to avoid unnecessary friction and collision between the members incurred by any sway of the forehead support 12, and thereby prolongs the service life of the members and facilitates packaging and handling of the face mask assembly.

When the face mask assembly is not worn by the wearer, the elastic member 16 may work with the spring or protruding post 123 to jointly retain the forehead support 12 in original position, prevent the forehead support 12 to get loose and sway on the frame body 11, and limit the swinging range of the forehead support 12.

In the face mask assembly in the embodiment of the present invention, the forehead support 12 is connected to the frame body 11 via the connecting member 13, and the connecting member 13 can be connected to the frame body 11 and then swing in the air intake port 112 arranged on the frame body 11. When the forehead support 12 is actuated, the forehead support 12 will actuate the connecting member 13 to swing synchronously. The wearer may swing the forehead support 12 according to the height of his/her forehead so as to adjust the position of the forehead support 12. Such an adjusting method is simple, convenient and quick.

When the forehead support 12 swings by small amplitude to get close to the connecting member 13, the part of the forehead support 12 where the upper headgear hook 121 is arranged will swing by greater amplitude. Therefore, the forehead support 12 has a greater adjustment range to meet the wearing demand of different wearers with different forehead heights. Within the swinging range of the forehead support 12, the forehead support 12 supports stepless adjustment of the distance from the forehead support 12 to the forehead of the wearer. Thus, the applicability of the forehead support 12 is widened, and the demand of different wearers for different heights of the forehead support 12 is met.

In other embodiments, the first end of the connecting member 13 may be flexibly connected to the frame body 11, and the second end of the connecting member 13 may be fixedly connected to the forehead support 12, so that the forehead support 12 can swing. For example, the first end of the connecting member 13 may be made of a flexible material, so that the forehead support 12 can swing after the connecting member 13 is connected to the frame body 11. The connecting member 13 may be formed with the frame body 11 integrally, or the second end of the connecting member 13 may be connected to the frame body 11 via a flexible sleeve made of a flexible material.

While the present invention is described above with reference to some preferred embodiments, various modifications or equivalent component replacements can be made without departing from the scope of the present invention. Especially, the technical features mentioned in the embodiments can be combined in any way, as long as there is no structural confliction. The present invention is not limited to the specific embodiments disclosed herein, but is intended to encompass all technical schemes falling into the scope defined by the attached claims.

The invention claimed is:

1. A face mask assembly, comprising:
   a frame, comprising a frame body provided with an air intake port;
   an elbow assembly, comprising an air intake tube;
   a connecting member, comprising a first end and a second end arranged opposite to each other, the first end is directly hinged to the air intake port so that the connecting member is able to swing freely in the air intake port based on the hinge point between the air intake port and the first end and in a certain angle range in an axial direction of the air intake port, and the second end having a forehead support directly fixed thereon and configured to communicate with the air intake tube, an end of the air intake tube connected with the second end of the connecting member is provided with an annular groove, and the forehead support and the second end of the connecting member are sleeved in the annular groove and relatively fixed;
   the forehead support comprising a fitting part that is adapted to be fitted to a forehead, a mounting part fixedly mounted on the second end of the connecting member, so that the forehead support is connected to the frame body via the connecting member, and a connecting part connecting the fitting part and the mounting part;
   wherein the mounting part of the forehead support has a mounting hole, and the second end of the connecting member is fitted in the mounting hole, the forehead support is able to swing due to the connecting member being swung.

2. The face mask assembly according to claim 1, wherein an outer surface of the first end of the connecting member is a truncated spherical surface, and the air intake port is ball-hinged to the first end of the connecting member.

3. The face mask assembly according to claim 2, wherein the first end of the connecting member includes a first limiting part arranged on the outer surface, an inner surface of the air intake port includes a second limiting part fitted with the first limiting part, and the first limiting part and the second limiting part are fitted with each other to prevent the connecting member from rotating within the air intake port around an axis of the air intake port.

4. The face mask assembly according to claim 3, wherein the first limiting part is a first flat surface or concave spherical surface, the second limiting part is a second flat surface fitted with the first flat surface or a convex spherical surface fitted with the concave spherical surface.

5. The face mask assembly according to claim 3, wherein the first limiting part is a groove extending in an axial direction of the connecting member; the second limiting part is a first protrusion arranged on the inner surface of the air intake port and fitted with the groove.

6. The face mask assembly according to claim 5, wherein the outer surface of the first end of the connecting member is arranged with a second protrusion extending in a circumferential direction around an axis of the truncated spherical surface, the second protrusion is disposed on one side or two sides of the groove.

7. The face mask assembly according to claim 1, wherein a limiting member is arranged on a surface of the forehead support that faces the frame body near a lower end of the mounting part.

8. The face mask assembly according to claim 7, wherein the limiting member is a spring.

9. The face mask assembly according to claim 1, wherein the face mask assembly further comprising an elastic member arranged in a clearance formed between the connecting part of the forehead support and the frame body.

\* \* \* \* \*